United States Patent [19]

Yano et al.

[11] Patent Number: 5,055,491
[45] Date of Patent: Oct. 8, 1991

[54] CARBOXYLIC ACID ESTERS, METHODS FOR PRODUCING THEM AND INSECTICIDES AND/OR ACARICIDES CONTAINING THEM AS AN ACTIVE INGREDIENT

[75] Inventors: Toshihiko Yano, Ashiya; Takao Ishiwatari, Minoo; Hiroko Sekihachi, Toyonaka; Noritada Matsuo, Itami; Tohei Takagaki, Takarazuka; Akiko Kakimizu, Nishinomiya, all of Japan

[73] Assignee: Sumitomo Chemical Company, Limited, Osaka, Japan

[21] Appl. No.: 503,664

[22] Filed: Apr. 2, 1990

[30] Foreign Application Priority Data

Apr. 10, 1989 [JP] Japan .................... 1-91555

[51] Int. Cl.$^5$ ............................. A01N 53/00
[52] U.S. Cl. ....................... 514/531; 560/124
[58] Field of Search .................. 560/124; 514/531

[56] References Cited

U.S. PATENT DOCUMENTS

| | | | |
|---|---|---|---|
| 4,024,163 | 5/1977 | Elliott | 560/124 |
| 4,118,505 | 10/1978 | Kitamura et al. | 514/531 |
| 4,489,093 | 12/1984 | Martel | 560/124 |
| 4,714,712 | 12/1987 | Matsuo et al. | 424/275 |
| 4,883,806 | 11/1989 | Martel | 560/124 |

FOREIGN PATENT DOCUMENTS

| | | | |
|---|---|---|---|
| 114012 | 7/1984 | European Pat. Off. | 560/124 |
| 344768 | 12/1989 | European Pat. Off. | 560/124 |
| 57-11943 | 1/1982 | Japan. | |
| 57-125447 | 8/1982 | Japan. | |
| 59-118742 | 7/1984 | Japan. | |

OTHER PUBLICATIONS

Elliott, Chem. Soc. Rev., 7, pp. 473–505 (1978).

*Primary Examiner*—Michael L. Shippen
*Attorney, Agent, or Firm*—Stevens, Davis, Miller & Mosher

[57] ABSTRACT

This invention relates to novel carboxylic acid esters represented by the formula (I) below, methods for their production and insecticides and/or acaricides containing them as an active ingredient,

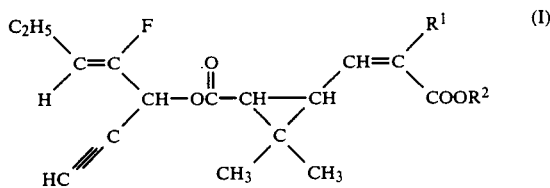

wherein $R^1$ represents a hydrogen atom, a fluorine atom or a methyl group; and $R^2$ represents a $C_{1-5}$ alkyl group, a $C_{3-6}$ cycloalkyl group, a $C_{3-6}$ alkenyl group, a $C_{3-6}$ alkynyl group or a $C_{1-5}$ haloalkyl group.

14 Claims, No Drawings

CARBOXYLIC ACID ESTERS, METHODS FOR PRODUCING THEM AND INSECTICIDES AND/OR ACARICIDES CONTAINING THEM AS AN ACTIVE INGREDIENT

The present invention relates to a novel carboxylic acid ester, a method for its production and insecticides and/or acaricides containing it as an active ingredient.

Hitherto, the ester compounds, for example, described in U.S. Pat. No. 4,118,505 (JP-B-55-42,045), FR 2,491,060, EP 41,021 A3 (JP-A-57-11,943), EP 50,534 Al (JP-A-57-126,447), EP 114,012A (JP-A-59-118,742) and U.S. Pat. No. 4,714,712 (JP-A-61-280,453) are known to have an 4,714,712 (JP-A-61-280,453) are known to have an insecticidal and/or acaricidal activity.

However, the insecticidal and/or acaricidal effect of the compounds is not always said to be satisfactory.

In view of the situation like this, the present inventors have extensively studied to develop a compound having excellent insecticidal and/or acaricidal activity, and as a result, have found that an ester compound represented by the formula (I) (hereinafter referred to as present compound) has a very high insecticidal and/or acaricidal activity

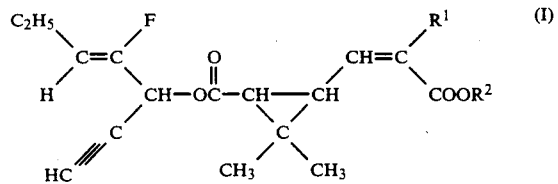

wherein $R^1$ represents a hydrogen atom, a fluorine atom or a methyl group; and $R^2$ represents a $C_{1-5}$ alkyl group, a $C_{3-6}$ cycloalkyl group, a $C_{3-6}$ alkenyl group, a $C_{3-6}$ alkynyl group or a $C_{1-5}$ haloalkyl group.

The present inventors thus attained to the present invention.

The present compounds have excellent properties as follows:

(1) Act on various insect and/or acarine pests very rapidly and also with a high insecticidal and/or acaricidal activity.

(2) Have a high insecticidal and/or acaricidal effect especially in the form of an oil spray or aerosol.

(3) Have a very high activity as a fumigant, smoking formulation or volatile formulation.

(4) Exhibit an excellent effect on insect and/or acarine pests resistant to organophosphorus or carbamate pesticides.

Among the present compounds, preferred ones are those in which $R^2$ is a $C_{1-5}$ alkyl group, a cyclopropyl group, a $C_{3-4}$ alkenyl group, a $C_{3-4}$ alkynyl group or a $C_{1-4}$ haloalkyl group. Of these compounds, those in which $R^1$ is a hydrogen atom or a fluorine atom are more preferred. Particularly, those in which $R^1$ is a hydrogen atom or a fluorine atom, and $R^2$ is a methyl group, an ethyl group, a n-propyl group, an isopropyl group, a tert-butyl group, a cyclopropyl group, an allyl group, a propargyl group, a 2-chloroethyl group or a 2-fluoroethyl group are further more preferred, and those in which $R^1$ is a hydrogen atom or a fluorine atom, and $R^2$ is a methyl group, an ethyl group, a n-propyl group, an isopropyl group, a tert-butyl group or a cyclopropyl group are most preferred.

Referring to typical compounds of the preferred compounds, there are mentioned for example 1-ethynyl-2-fluoro-2-pentenyl 2,2-dimethyl-3-(2-ethoxycarbonyl-2-fluorovinyl)cyclopropanecarboxylate, 1-ethynyl-2-fluoro-2-pentenyl 2,2-dimethyl-3-(2-methoxycarbonyl-2-fluorovinyl)cyclopropanecarboxylate, 1-ethynyl-2-fluoro-2-pentenyl 2,2-dimethyl-3-(2-isopropoxycarbonyl-2-fluorovinyl)cyclopropanecarboxylate, 1-ethynyl-2-fluoro-2-pentenyl 2,2-dimethyl-3-(2-tert-butoxycarbonyl-2-fluorovinyl)cyclopropanecarboxylate, 1-ethynyl-2-fluoro-2-pentenyl 2,2-dimethyl-3-(2-n-propoxycarbonyl-2-fluorovinyl)cyclopropanecarboxylate, 1-ethynyl-2-fluoro-2-pentenyl 2,2-dimethyl-3-(2-cyclopropoxycarbonyl-2-fluorovinyl)cyclopropanecarboxylate, 1-ethynyl-2-fluoro-2-pentenyl 2,2-dimethyl-3-(2-ethoxycarbonylvinyl)cyclopropanecarboxylate, 1-ethynyl-2-fluoro-2-pentenyl 2,2-dimethyl-3-(2-methoxycarbonylvinyl)cyclopropanecarboxylate, 1-ethynyl-2-fluoro-2-pentenyl 2,2-dimethyl-3-(2-isopropoxycarbonylvinyl)cyclopropanecarboxylate, 1-ethynyl-2-fluoro-2-pentenyl 2,2-dimethyl-3-(2-cyclopropoxycarbonylvinyl)cyclopropanecarboxylate, (S)-1-ethynyl-2-fluoro-2-pentenyl (1R, cis, E)-2,2-dimethyl-3-(2-ethoxycarbonyl-2-fluorovinyl)cyclopropanecarboxylate.

The present compounds can be produced by reacting a 4-fluoro-3-hydroxy-4-heptene-1-yne represented by the formula (II),

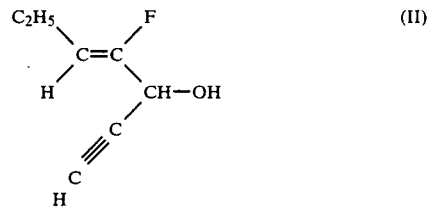

with a carboxylic acid halide represented by the formula (III),

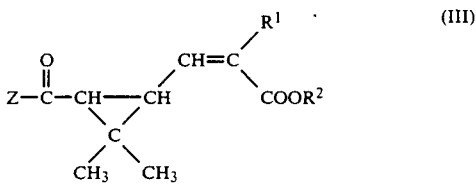

wherein Z represents a halogen atom and $R^1$ and $R^2$ represent the same meanings as described above, if necessary, in the presence of a suitable inert solvent, reaction auxiliary reagent or catalyst.

The compounds of the present invention represented by the formula (I) have optical isomers due to the asymmetric carbon atoms on the acid moiety and the alcohol moiety and stereoisomers due to the acid moiety, and all of these isomers are within the scope of the present invention.

In the compounds of the present invention, the optical isomers wherein the acid moiety has an absolute configuration of (1R) and/or the alcohol moiety has an absolute configuration of (S) have very high insecticidal activities.

The present compounds are produced by reacting a carboxylic acid halide represented by the foregoing formula (III), preferably an acid chloride, with an alcohol represented by the foregoing formula (II) at from −30° to 100° C. for from 30 minutes to 20 hours in an inert solvent and in the presence of an acid-binding agent. The inert solvent includes for example benzene, toluene, hexane, diethyl ether, etc., and the acid-binding agent includes for example pyridine, triethylamine, etc. Referring to the amounts of the reagents used in this reaction, the carboxylic acid halide is used in an amount of usually from 0.9 to 1.5 equivalents, preferably from 0.95 to 1.1 equivalents based on 1 equivalent of the alcohol represented by the formula (II), and the acid-binding agent is used in an amount of usually from 1.0 to 2.0 equivalents, preferably from 1.0 to 1.2 equivalents based on the same. After completion of the reaction, usual work-up is applied, and if necessary, it suffices to apply purification by chromatography, etc.

Example of the present compounds which can be produced by the above method will be given in Table 1.

TABLE 1

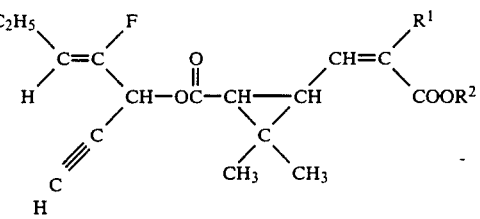

| $R^1$ | $R^2$ | Alcohol moiety | Acid moiety |
|---|---|---|---|
| F | $C_2H_5$ | S | 1R-cis-E |
| F | $C_2H_5$ | RS | 1R-trans-E |
| F | $C_2H_5$ | S | 1R-trans-Z |
| F | $C_2H_5$ | RS | 1R-cis-E |
| F | $C_2H_5$ | RS | 1R-trans-Z |
| F | $CH_3$ | S | 1R-cis-E |
| F | $CH_3$ | RS | 1R-cis-E |
| F | $n$-$C_3H_7$ | S | 1R-cis-E |
| F | $n$-$C_3H_7$ | RS | 1R-cis-E |
| F | $i$-$C_3H_7$ | S | 1R-cis-E |
| F | $t$-$C_4H_9$ | S | 1R-cis-E |
| F | $n$-$C_5H_{11}$ | S | 1R-cis-E |
| F | ◁ | S | 1R-cis-E |
| F | $CH_2CH=CH_2$ | S | 1R-cis-E |
| F | $CH_2C\equiv CH$ | S | 1R-cis-E |
| F | $CH_2CH_2F$ | S | 1R-cis-E |
| F | $CH_2Cl$ | S | 1R-cis-E |
| F | $CH_2CH_2Cl$ | S | 1R-cis-E |
| H | $C_2H_5$ | S | 1R-cis-Z |
| H | $CH_3$ | S | 1R-cis-Z |
| $CH_3$ | $C_2H_5$ | S | 1R-cis-Z |
| F | $CH(CF_3)_2$ | S | 1R-cis-E |
| F | $CH_2CF_3$ | S | 1R-cis-E |
| $CH_3$ | $CH_3$ | S | 1R-cis-Z |
| F | $C_2H_5$ | RS | 1RS-cis,trans-E/Z |
| F | $C_2H_5$ | RS | 1RS-cis,trans-E |
| F | $C_2H_5$ | RS | 1RS-cis-E/Z |
| F | $C_2H_5$ | RS | 1RS-cis-E |
| F | $C_2H_5$ | RS | 1RS-trans-Z |

TABLE 1-continued

| $R^1$ | $R^2$ | Alcohol moiety | Acid moiety |
|---|---|---|---|
| F | $C_2H_5$ | RS | 1R-cis,trans-E/Z |
| F | $C_2H_5$ | RS | 1R-cis,trans-E |
| F | $C_2H_5$ | RS | 1RS-cis-E/Z |
| F | $C_2H_5$ | S | 1RS-cis,trans-E/Z |
| F | $C_2H_5$ | S | 1RS-cis,trans-E |
| F | $C_2H_5$ | S | 1RS-cis-E/Z |
| F | $C_2H_5$ | S | 1RS-cis-E |
| F | $C_2H_5$ | S | 1RS-trans-Z |
| F | $C_2H_5$ | S | 1R-cis,trans-E/Z |
| F | $C_2H_5$ | S | 1R-cis,trans-E |
| F | $C_2H_5$ | S | 1R-cis-E/Z |
| F | $CH_3$ | RS | 1R-cis-E |
| F | $CH_3$ | S | 1R-cis-E |
| F | $CH_3$ | S | 1R-trans-Z |
| F | $i$-$C_3H_7$ | RS | 1RS-cis-E |
| F | $i$-$C_3H_7$ | RS | 1R-cis-E |
| F | $i$-$C_3H_7$ | S | 1RS-cis-E |
| F | $i$-$C_3H_7$ | S | 1R-trans-Z |
| F | $t$-$C_4H_9$ | RS | 1RS-cis-E |
| F | $t$-$C_4H_9$ | RS | 1R-cis-E |
| F | $t$-$C_4H_9$ | S | 1RS-cis-E |
| F | $t$-$C_4H_9$ | S | 1R-trans-Z |
| F | $n$-$C_3H_7$ | RS | 1RS-cis-E |
| F | $n$-$C_3H_7$ | S | 1RS-cis-E |
| F | $n$-$C_3H_7$ | S | 1R-trans-Z |
| F | ◁ | RS | 1RS-cis-E |
| F | ◁ | RS | 1R-cis-E |
| F | ◁ | S | 1RS-cis-E |
| F | ◁ | S | 1R-trans-Z |
| H | $CH_3$ | RS | 1R-cis-Z |
| H | $CH_3$ | S | 1RS-cis-Z |
| H | $CH_3$ | S | 1R-trans-E |
| H | $C_2H_5$ | RS | 1R-cis-Z |
| H | $C_2H_5$ | S | 1RS-cis-Z |
| H | $C_2H_5$ | S | 1R-trans-E |
| H | $i$-$C_3H_7$ | RS | 1R-cis-Z |
| H | $i$-$C_3H_7$ | S | 1RS-cis-Z |
| H | $i$-$C_3H_7$ | S | 1R-cis-Z |
| H | $i$-$C_3H_7$ | S | 1R-trans-E |
| H | ◁ | RS | 1R-cis-Z |

TABLE 1-continued

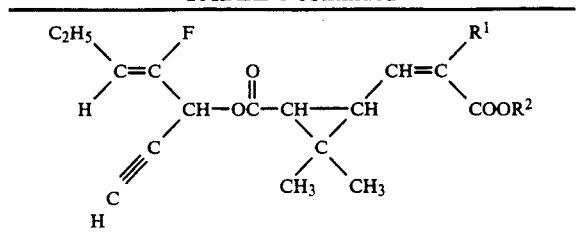

| R¹ | R² | Alcohol moiety | Acid moiety |
|---|---|---|---|
| H | △ | S | 1RS-cis-Z |
| H | △ | S | 1R-cis-Z |
| H | △ | S | 1R-trans-E |
| F | ◇ | S | 1R-cis-E |
| F | CF₃–CH–CH₃ | S | 1R-cis-E |
| F | △ | S | 1R-cis-E |
| CH₃ | C₂H₅ | S | 1R-trans-E |
| CH₃ | i-C₃H₇ | S | 1R-cis-Z |
| CH₃ | △ | S | 1R-cis-Z |
| CH₃ | n-C₃H₇ | S | 1R-cis-Z |
| CH₃ | t-C₄H₉ | S | 1R-cis-Z |
| CH₃ | △ | S | 1R-cis-Z |
| CH₃ | —CH₂CF₃ | S | 1R-cis-Z |
| CH₃ | CF₃–CH–CH₃ | S | 1R-cis-Z |
| CH₃ | CH₃ | S | 1R-trans-E |
| CH₃ | i-C₃H₇ | S | 1R-trans-E |
| CH₃ | △ | S | 1R-trans-E |

TABLE 1-continued

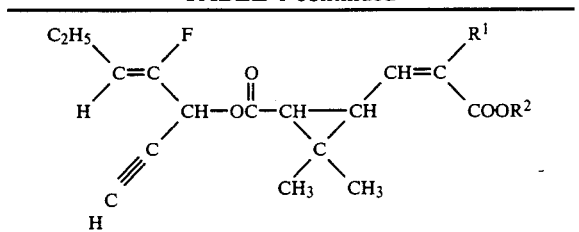

| R¹ | R² | Alcohol moiety | Acid moiety |
|---|---|---|---|
| CH₃ | n-C₃H₇ | S | 1R-trans-E |
| CH₃ | t-C₄H₉ | S | 1R-trans-E |
| CH₃ | △ | S | 1R-trans-E |
| CH₃ | —CH₂CF₃ | S | 1R-trans-E |
| CH₃ | CF₃–CH–CH₃ | S | 1R-trans-E |
| H | n-C₃H₇ | S | 1R-cis-Z |
| H | t-C₄H₉ | S | 1R-cis-Z |
| H | △ | S | 1R-cis-Z |
| H | —CH₂CF₃ | S | 1R-cis-Z |
| H | CF₃–CH–CH₃ | S | 1R-cis-Z |
| H | CH₃ | RS | 1RS-cis-Z |
| H | C₂H₅ | RS | 1RS-cis-Z |
| H | i-C₃H₇ | RS | 1RS-cis-Z |
| H | △ | RS | 1RS-cis-Z |
| H | n-C₃H₇ | RS | 1RS-cis-Z |
| H | t-C₄H₉ | RS | 1RS-cis-Z |
| H | △ | RS | 1RS-cis-Z |
| H | —CH₂CF₃ | RS | 1RS-cis-Z |
| H | CF₃–CH–CH₃ | RS | 1RS-cis-Z |
| F | △ | RS | 1RS-cis-E |
| F | —CH₂CF₃ | RS | 1RS-cis-E |

TABLE 1-continued $$\underset{H}{\overset{C_2H_5}{\diagdown}}C=C\underset{\underset{\underset{H}{\overset{|}{C}}}{\overset{|}{C}}}{\overset{F}{\diagup}}\underset{CH-OC-CH-CH}{\overset{O}{\overset{\|}{\diagdown}}}\underset{\underset{CH_3}{\overset{|}{C}}\underset{CH_3}{\diagdown}}{\diagdown}CH=C\underset{COOR^2}{\overset{R^1}{\diagup}}$$

| $R^1$ | $R^2$ | Alcohol moiety | Acid moiety |
|---|---|---|---|
| F | −C(CF$_3$)(CH$_3$) | RS | 1RS-cis-E |
| F | cyclopropyl | RS | 1RS-cis-E |
| F | −CH$_2$CF$_3$ | RS | 1RS-cis-E |
| F | −C(CF$_3$)(CH$_3$) | RS | 1RS-cis-E |
| F | cyclopropyl | S | 1RS-cis-E |
| F | −CH$_2$CF$_3$ | S | 1RS-cis-E |
| F | −C(CF$_3$)(CH$_3$) | S | 1RS-cis-E |

For insects and acarines against which the present compounds are particularly efficacious, there are given the following:

Hemiptera: Planthoppers (Delphacidae) such as smaller brown planthopper (*Laodelphax striatellus*), brown planthopper (*Nilaparvata lugens*) and whitebacked rice planthopper (*Sogatella furcifera*); leafhoppers (*Deltocephalidae*) such as green rice leafhoppers (*Nephotettix cincticeps, Nephotettix nigropictus* and *Nephotettix virescens*); aphids (Alphididae) bugs; whiteflies (Aleyrodidae); scales; lace bugs (Tingidae); and psyllids (Psyllidae); etc.

Lepidoptera: Pyralidae such as rice stem borer (*Chilo suppressalis*), rice leafroller (*Cnaphalocrocis medinalis*) and Indian meal moth (*Plodia interpunctella*); Noctuidae such as tobacco cutworm (*Spodoptera litura*), rice armyworm (i Pseudaletia separata), cabbage armyworm (*Mamestra brassicae*), turnip cutworm (*Agrotis segetum*), black cutworm (*Agrotis ipsilon*) and Heliothis spp.; Pieridea such as common cabbageworm (*Pieris rapae crucivora*); Tortricidae such as Adoxophyes spp. and Grapholita spp.; Carposinidae; Lyonetiidae; Lymantriidae; Yponomeutidae such as diamondback moth (*Plutella xylostella*); Tineidae such as casemaking clothes moth (*Tinea pellionella*) and webbing clothes moth (*Tineola bisselliella*); etc.

Diptera: Culex spp. such as common mosquito (*Culex pipiens pallens*) and *Culex tritaeniorhynchus;* Aedes spp. such as *Aedes aegypti, Aedes albopictus* and *Aedes togoi;* Anopheles spp. such as *Anopheles sinensis* and *Anopheles stephensi;* Chironomidae; Muscidae such as housefly (*Musca domestica*), little housefly (*Fannia canicularis*) and false stablefly (*Muscina stabulans*); Calliphoridae; Sarcophagidae; Anthomyiidae such as seedcorn maggot (*Delia platura*) and onion maggot (*Delia antigua*); Tephritidea; Drosophilidae; Psychodidae; black flies (Simuliidae); Tabanidae and stable flies (Stomoxyidae); etc.

Coleoptera: Scarabaeidae such as cupreous chafer (*Anomala cuprea*) and soybean beetle (*Anomala rufocuprea*); weevils (*Curculionidae*) such as maize weevil (*Sitophilus zeamais*) and ricewater weevil (*Lissorhoptrus oryzophilus*); Tenebrionidae such as yellow mealworm (*Tenebrio molitor*) and red flour beetle (*Tribolium castaneum*); Chrysomelidae such as western corn rootworm (*Diabrotica virgifera*), southern corn rootworm (*Diabrotica undecimpunctaca howardi*), striped flea beetle (*Phyllotreta striolata*) and cucurbit leaf beetle (*Aulacophora femoralis*); Anobiidae; ladybirds (Coccinellidae) such as twenty-eight-spotted ladybird (*Henosepilachna viqintioctopunctata*); powder post beetles (Lyctidae); false powderpost beetles (Bostrychidae); Cerambycidae; Staphylinidae such as robe beetle (*Paederus fuscipes*); and Dermestidae such as varied carpet beetle (*Anthrenus verbasci*); etc.

Dictyoptera: Blattelidae such as German cockroach (*Blattella germanica*); and Blattidae such as smoky-brown cockroach (*Periplaneta fuliqinosa*), American cockroach (*Periplaneta americana*), brown cockroach (*Periplaneta brunnea*) and oriental cockroach (*Blatta orientalis*); etc.

Thysanoptera: *Thrips palmi* and flower thrips (*Thrips hawaiiensis*); etc.

Hymenoptera: ants (Formicidae); hornests (Vespidae); bethylid wasps (Bethylidae); and sawflies (*Tenthredinidae*) such as cabbage sawfly (*Athalia rosae ruficornis*); etc.

Orthoptera: mole crickets (Gryllotalpidae); and grasshoppers (Acrididae); etc.

Siphonaptera: Pulicidae such as *Pulex irritans;* etc.

Anoplura: Pediculidae such as *Pediculus humanus capitis;* and *Pthirus pubis;* etc.

Isoptera: *Reticulitermes speratus;* and *Coptotermes formosanus;* etc.

Acarina: Tetranychidae such as carmine spider mite (*Tetranychus cinnabarinus*), two-spotted spider mite (*Tetranychus urticae*), Kanzawa spider mite (*Tetranychus kanzawai*), citrus red mite (*Panonychus citri*) and European red mite (*Panonychus ulmi*); Ixodidae such as *Boophilus microplus;* Dermanyssidae; and other mites associated with house dust and stored food such as Acaridae, Pyroglyphidae, and Cheyletidae; etc.

The present compounds exhibit a particularly excellent insecticidal and/or acaricidal effect against the foregoing insect and/or acarine pests in the forms of a fumigant, volatile formulation, smoking formulation, oil spray, aerosol, etc.

When the present compounds are used as an active ingredient for insecticides and/or acaricides, they may be used as they are without adding any other ingredients. Usually, however, they are formulated into oil sprays, emulsifiable concentrates, wettable powders, flowable concentrates (e.g. water-based suspension formulations, water-based emulsion formulations), granules, dusts, aerosols, heating fumigants (e.g. mosquito coils, electric mosquito mats, electric non-mat formulation i.e. heating fumigation of such a form that a part of a porous absorptive wick is dipped in an insecticidal solution to allow it to absorb the solution and said wick is indirectly heated at the top to fumigate the absorbed insecticidal solution), heating smoking formulations (e.g. self-burning-type smoking formulations, chemical reaction-type smoking formulations, electric heating-type smoking formulations), volatile formulations, foggings, ULV formulations, poisonous baits, etc. by mixing with solid carriers, liquid carriers, gaseous carriers, baits, etc. or impregnating into base materials (e.g. mosquito coil carriers, mats) and if necessary, by additionally adding surface active agents and other auxiliaries for formulation.

These preparations contain the present compounds as an active ingredient in an amount of, usually, from 0.001 to 95% by weight.

The solid carriers used in the formulation include for example fine powders or granules of clays (e.g. kaolin clay, diatomaceous earth, synthetic hydrated silicon dioxide, bentonite, Fubasami clay, terra alba), talcs, ceramics, other inorganic minerals (e.g. sericite, quartz, sulfur, activated carbon, calcium carbonate, hydrated silica), chemical fertilizers (e.g. ammonium sulfate, ammonium phosphate, ammonium nitrate, urea, ammonium chloride), etc. The liquid carriers include for example water, alcohols (e.g. methanol, ethanol), ketones (e.g. acetone, methyl ethyl ketone, cyclohexanone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethyl sulfoxide, vegetable oils (e.g. soybean oil, cotton seed oil), etc. The gaseous carriers, i.e. a propellant, include for example freon gas, butane gas, LPG (liquefied petroleum gas), dimethyl ether, carbon dioxide gas, etc.

The surface active agents include for example alkyl sulfates, alkylsulfonates, alkylarylsulfonates, alkyl aryl ethers and their polyoxyethylenized products, polyethylene glycol ethers, polyhydric alcohol esters, sugar alcohol derivatives, etc.

The auxiliaries for formulation such as fixing agents, dispersing agents, etc. include for example casein, gelatin, polysaccharides (e.g. starch powder, gum arabic, cellulose derivatives, alginic acid), lignin derivatives, bentonite, saccharides, synthetic water-soluble high polymers (e.g. polyvinyl alcohol, polyvinyl pyrrolidone, polyacrylic acids), etc. The stabilizing agents include for example PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surface active agents, fatty acids and their esters, etc.

The base material for mosquito coils includes for example mixtures of a vegetable powder (e.g. wood powder, Pyrethrum marc) with a binder (e.g. Tabu powder, starch, gluten).

The base material for electric mosquito mats includes for example plate-like pressed products of fibrils of cotton linters or a mixture of cotton linters and pulp.

The base material for self-burning-type smoking formulations includes for example burning.heat-generating agents such as nitrates, nitrites, guanidine salts, potassium chlorate, nitrocellulose, ethyl cellulose, wood powders, etc.; pyrolysis-promoting agents such as alkali metal salts, alkaline earth metal salts, dichromates, chromates, etc.; oxygen-supplying agents such as potassium nitrate, etc.; burning-supporting agents such as melamine, wheat starch, etc.; extenders such as diatomaceous earth, etc.; and binders such as synthetic pastes, etc.

The base material for chemical reaction-type smoking formulations includes for example heat-generating agents such as the sulfides, polysulfides, hydrosulfides or salt hydrates of alkali metals, calcium oxide, etc.; catalyzing agents such as carbonaceous substances, iron carbide, activated clay, etc.; organic foaming agents such as azodicarbonamide, benzenesulfonyl hydrazide, dinitrosopentamethylenetetramine, polystyrene, polyurethane, etc.; fillers such as natural fiber pieces, synthetic fiber pieces, etc.

The base material for electric heating-type smoking formulations includes for example porous ceramic plates, pulp, asbestos, porous glass material, etc.

The base material for the poisonous baits includes for example bait components (e.g. grain powders, vegetable essential oils, saccharides, crystalline cellulose), antioxidants (e.g. dibutylhydroxytoluene, nordihydroguaiaretic acid), preservatives (e.g. dehydroacetic acid), attractants (e.g. cheese perfume, onion perfume, peanut oil), etc. Further, red pepper powders etc. also are included as an agent for preventing children from eating by mistake.

The flowable concentrates (water-based suspension formulations or water-based emulsion formulations) are generally obtained by finely dispersing 1 to 75% of the active ingredient compounds in water containing 0.5 to 15% of a dispersing agent, 0.1 to 10% of a suspension auxiliary (e.g. protective colloids, compounds giving a thixotropic property) and 0 to 10% of a suitable auxiliary (e.g. defoaming agents, anti-corrosives, stabilizing agents, spreading agents, penetration auxiliaries, antifreezing agents, anti-bacterial agents, antimolding agents). It is also possible to obtain oil-based suspension formulations by replacing water by an oil in which the active ingredient compounds are almost insoluble. The protective colloids include for example gelatin, casein, gums, cellulose ethers, polyvinyl alcohol, etc., and the compounds giving a thixotropic property include for example bentonite, aluminum magnesium silicate, xanthane gum, polyacrylic acid, etc.

The preparations thus obtained are used as they are or diluted with water, etc. Further, they may be used mixed with other insecticides, acaricides, nematocides, soil-pest controlling agents, repellents, fungicides, herbicides, plant growth regulators, synergists, fertilizers, soil improvers, etc., or may be used simultaneously with these chemicals without mixing.

When the present compounds are used as an active ingredient for agricultural insecticides and/or acaricides, their dosage rate is usually from 5 to 500 g/10 ares. When the emulsifiable concentrates, wettable powders, flowable concentrates, etc. are used diluted with water, the application concentration of the active ingredient is from 0.1 to 1000 ppm. The granules, dusts, etc. are used as they are without being diluted. When the present compounds are used as an active ingredient for household and public hygiene insecticides and/or acaricides, the emulsifiable concentrates, wettable powders, flowable concentrates, etc. are applied diluted with water to 0.1 to 10000 ppm, and the oil sprays, aerosols, fumigants, smoking formulations, volatile formulations, foggings, ULV formulations, poisonous baits, etc. are applied as they are.

Although any of these dosage rate and application concentration varies with the kind of preparations, when, where and how these preparations are applied, the kind of pests, the degree of damage, etc., they may be increased or decreased independently of the ranges explained above.

The present invention will be illustrated in more detail with reference to the following production examples, formulation examples and test examples, but it is not limited to these examples.

First, production examples for the present compounds will be shown.

PRODUCTION EXAMPLE 1

Production of the Present Compound (1)

134 Milligrams of (S)-4-fluoro-3-hydroxy-4-heptene-1-yne and 287 mg of (1R, cis, E)-2,2-dimethyl-3-(2-ethoxycarbonyl-2-fluorovinyl)cyclopropanecarboxylic acid chloride were dissolved in 5 ml of dry toluene, and 108 mg of pyridine was added dropwise thereto with ice-cooling. After the reaction solution was stirred overnight at room temperature, it was poured into a 5% hydrochloric acid and extracted with diethyl ether. The ether layer was successively washed with water and a saturated aqueous sodium chloride solution and dried over anhydrous magnesium sulfate. The solvent was removed under reduced pressure, and the residue obtained was treated by chromatography on silica gel (developing solvent, hexane:ethyl acetate=5:1) to obtain 290 mg of the desired compound.

$^1$H-NMR (Solvent, CDCl$_3$; δvalue) 1.02 (t, 3H) 1.20–1.53 (m, 9H) 1.85–2.5 (m, 3H) 2.56 (d, 1H) 2.65–3.06 (m, 1H) 4.30 (q, 2H) 5.20 (dt, 1H) 5.90 (dd, 1H) 6.31 (dd, 1H)

$^{19}$F-NMR (Solvent, CDCl$_3$; CF$_3$COOH as an external standard; δvalue) −48.53 (dds, 1F), −44.32 (d, 1F)

Some of the present compounds produced according to the foregoing methods will be shown in Table 2.

TABLE 2

| Compound No. | R$^1$ | R$^2$ | Alcohol moiety | Acid moiety | Refractive index (Na dry) (°C.) |
|---|---|---|---|---|---|
| (1) | F | C$_2$H$_5$ | S | 1R-cis-E | 1.4769 (20.0) |
| (2) | F | C$_2$H$_5$ | RS | 1R-trans-E | 1.4790 (23.0) |
| (3) | F | C$_2$H$_5$ | S | 1R-trans-Z | 1.4845 (23.0) |
| (4) | F | C$_2$H$_5$ | RS | 1R-cis-E | 1.4771 (23.0) |
| (5) | F | C$_2$H$_5$ | RS | 1R-trans-Z | 1.4836 (21.0) |
| (6) | F | CH$_3$ | S | 1R-cis-E | 1.4752 (23.0) |
| (7) | F | CH$_3$ | RS | 1R-cis-E | 1.4760 (23.0) |
| (8) | F | n-C$_3$H$_7$ | S | 1R-cis-E | 1.4772 (23.0) |
| (9) | F | n-C$_3$H$_7$ | RS | 1R-cis-E | 1.4781 (23.0) |
| (10) | F | i-C$_3$H$_7$ | S | 1R-cis-E | 1.4771 (23.0) |
| (11) | F | t-C$_4$H$_9$ | S | 1R-cis-E | 1.4782 (23.0) |
| (12) | F | n-C$_5$H$_{11}$ | S | 1R-cis-E | 1.4780 (23.0) |
| (13) | F | cyclopropyl | S | 1R-cis-E | 1.4739 (23.0) |
| (14) | F | CH$_2$CH=CH$_2$ | S | 1R-cis-E | 1.4835 (23.0) |
| (15) | F | CH$_2$C≡CH | S | 1R-cis-E | 1.4921 (23.0) |
| (16) | F | CH$_2$CH$_2$F | S | 1R-cis-E | 1.4711 (23.0) |
| (17) | F | CH$_2$Cl | S | 1R-cis-E | 1.5008 (23.0) |
| (18) | F | CH$_2$CH$_2$Cl | S | 1R-cis-E | 1.5019 (23.0) |
| (19) | H | C$_2$H$_5$ | S | 1R-cis-Z | 1.4870 (23.0) |
| (20) | H | CH$_3$ | S | 1R-cis-Z | 1.4815 (23.0) |
| (21) | CH$_3$ | C$_2$H$_5$ | S | 1R-cis-Z | 1.4851 (23.0) |
| (22) | F | CH(CF$_3$)$_2$ | S | 1R-cis-E | 1.4496 (23.0) |
| (23) | F | CH$_2$CF$_3$ | S | 1R-cis-E | 1.4581 (23.0) |
| (24) | CH$_3$ | CH$_3$ | S | 1R-cis-Z | 1.4837 (23.0) |

Production examples for insecticides and/or acaricides containing the present compounds as an active ingredient will be shown. In the following examples, parts are by weight.

FORMULATION EXAMPLE 1

Emulsifiable Concentrate

Ten parts of each of the present compounds (1) to (24) is dissolved in a mixture of 35 parts of xylene and 35 parts of dimethylformamide, and 14 parts of polyoxyethylene styrylphenyl ether and 6 parts of calcium dodecylbenzenesulfonate are added thereto. The resulting mixture is well stirred and mixed to obtain a 10% emulsifiable concentrate of each compound.

FORMULATION EXAMPLE 2

Wettable Powder

Twenty parts of the present compound (1), (19) or (21) is added to a mixture of 4 parts of sodium lauryl sulfate, 2 parts of calcium lignosulfonate, 20 parts of a fine powder of synthetic hydrated silicon dioxide and 54 parts of diatomaceous earth. The resulting mixture is stirred and mixed on a juice mixer to obtain a 20% wettable powder.

FORMULATION EXAMPLE 3

Granule

To 5 parts of the present compound (4), (20) or (24) are added 5 parts of sodium dodecylbenzenesulfonate, 30 parts of bentonite and 60 parts of clay, and the mixture is well stirred and mixed. A suitable amount of water is added to the mixture, and the mixture is further stirred, granulated on a granulator and air-dried to obtain a 5% granule.

FORMULATION EXAMPLE 4

Dust

One part of the present compound (6), (19) or (21) is dissolved in a suitable amount of acetone, and to the resulting solution are added 5 parts of a fine powder of synthetic hydrated silicon dioxide, 0.3 part of PAP and 93.7 parts of clay. The mixture is stirred and mixed on a juice mixer, and acetone is removed by vaporization to obtain a 1% dust.

FORMULATION EXAMPLE 5

Flowable Concentrate

Ten parts of the present compound (8), (20) or (24) is added to 40 parts of an aqueous solution containing 6 parts of polyvinyl alcohol, and the resulting mixture is stirred on a mixer to obtain a dispersion. To this dispersion are added 40 parts of an aqueous solution containing 0.05 part of xanthane gum and 0.1 part of aluminum magnesium silicate and then 10 parts of propylene glycol. The mixture is mildly stirred and mixed to obtain a 10% water-based emulsion formulation.

FORMULATION EXAMPLE 6

Oil Spray 0.1 Part of each of the present compounds (1) to (24) is dissolved in 99.9 parts of kerosene to obtain a 0.1% oil spray of each compound.

FORMULATION EXAMPLE 7

Oil-based Aerosol 0.2 Part of the present compound (1), (19) or (21), 0.1 part of d-Phenothrin, 59.7 parts of kerosene are mixed to prepare a solution. The solution is filled in an aerosol container. After mounting a valve portion on the container, 40 parts of a propellant (liquefied petroleum gas) is charged into the container under pressure through the valve portion to obtain an oil-based aerosol.

FORMULATION EXAMPLE 8

Water-based Aerosol 0.3 Part of the present compound (4), (20) or (24), 0.2 part of d-Phenothrin, 5 parts of xylene, 3.5 parts of kerosene and 1 part of an emulsifier (Atmos 300, a registered trademark of Atlas Chemical Co., Ltd.) are mixed to prepare a solution. The solution and 50 parts of pure water are filled in an aerosol container. After mounting a valve portion on the container, 40 parts of a propellant (liquefied petroleum gas) is charged into the container under pressure through the valve portion to obtain a water-based aerosol.

FORMULATION EXAMPLE 9

Mosquito Coil 0.3 Gram of each of the present compound (1) to (24) is dissolved in 20 ml of acetone, and the resulting solution is uniformly mixed with 99.7 g of a mosquito coil carrier (a mixture of Tabu powder, Pyrethrum marc and wood powder in a ratio of 4:3:3) with stirring. Thereafter, 120 ml of water is added, and the mixture is well kneaded, shaped into a mosquito coil and dried. Thus, a mosquito coil of each compound is obtained.

FORMULATION EXAMPLE 10

Electric Mosquito Mat 0.4 Gram of each of the present compound (1) to (24) and 0.4 g of piperonyl butoxide are dissolved in acetone, and the total volume of the solution is made up to 10 ml with acetone. Thereafter, 0.5 ml of this solution is uniformly impregnated into a base material for electric mat, which is a plate-like pressed product of fibrils of a mixture of cotton linters and pulp, having a size of 2.5 cm $\times$ 1.5 cm $\times$ 0.3 cm (thick). Thus, an electric mosquito mat formulation of each compound is obtained.

FORMULATION EXAMPLE 11

Heating Smoking Formulation

100 Milligrams of the present compound (8), (20) or (24) is dissolved in a suitable amount of acetone and impregnated into a porous ceramic plate having a size of 4.0 cm $\times$ 4.0 cm $\times$ 1.2 cm (thick) to obtain a heating smoking formulation.

Test examples on an insecticidal and/or acaricidal method using the present compounds will be shown below. The present compounds are shown by Compound Nos. in Table 2, and compounds used as a reference are shown by compound symbols in Table 3.

TABLE 3

| Compound Symbol | Structural formula | Remarks |
| --- | --- | --- |
| (A) | $(CH_3O)_2\overset{\overset{S}{\|\|}}{P}SCHCOOC_2H_5$<br>$\quad\quad\quad\quad\quad\|$<br>$\quad\quad\quad\quad CH_2COOC_2H_5$ | Malathion |

TABLE 3-continued

| Compound Symbol | Structural formula | Remarks |
|---|---|---|
| (B) | [structure with COOCH₃] | Compound No. 26 of U.S. Pat. No. 4,118,505 corresponding to JP-B-55-42045 |
| (C) | [structure with F, COOC₂H₅] | Compound No. 18 of EP-114,012A corresponding to JP-A-59-118742 |
| (D) | [structure with F, H, COOCH₃] | Compound No. 28 of the same patent application |
| (E) | [structure with F, F, COOC₂H₅] | Compound No. 31 of the same patent application |
| (F) | [structure with H, COOCH(CH₃)₂] | Compound No. 45 of the same patent application |
| (G) | [structure with F, Cl, Cl] | Compound No. 1 of U.S. Pat. No. 4714712 corresponding to JP-A-61-280453 |
| (H) | [structure with F] | Compound No. 2 of the same patent application |

TEST EXAMPLE 1

The emulsifiable concentrates of the following present compounds obtained according to Formulation example 1 were each diluted 200 times with water (corresponding to 500 ppm), and 2 ml of the aqueous dilute solution was impregnated into 13 g of artificial diet for tobacco cutworm (*Spodoptera litura*). The artificial diet were put in a polyethylene cup of 11 cm in diameter, and then 10 fourth instar larvae of tobacco cutworm were liberated in the cup. After six days, the dead and alive of the larvae were examined to obtain a mortality. This test was repeated twice The results are shown in Table 4.

TABLE 4

| Test compound | Mortality (%) |
|---|---|
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (13) | 100 |
| (14) | 100 |
| (15) | 100 |
| (16) | 100 |
| (17) | 100 |

TABLE 4-continued

| Test compound | Mortality (%) |
|---|---|
| (18) | 100 |
| (19) | 100 |
| (20) | 100 |
| (21) | 100 |
| (22) | 100 |
| (23) | 100 |
| (24) | 100 |
| No treatment | 5 |

TEST EXAMPLE 2

The emulsifiable concentrates of the following present compounds and the reference compound A obtained according to Formulation example 1 were each diluted 200 times with water (corresponding to 500 ppm), and rice seedlings (length, about 12 cm) were dipped for 1 minute in the aqueous dilute solution. After air-drying, the rice seedlings were put in a test tube, and 10 adults of resistant-strain green rice leafhopper (*Nephotettix cincticeps*) were liberated in the test tube. After one day, the dead and alive of the adults were examined to obtain a mortality. This test was repeated twice The results are shown in Table 5.

TABLE 5

| Test compound | Mortality (%) |
|---|---|
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (13) | 100 |
| (14) | 100 |
| (15) | 100 |
| (16) | 100 |
| (17) | 100 |
| (18) | 100 |
| (19) | 100 |
| (20) | 100 |
| (21) | 100 |
| (22) | 100 |
| (23) | 100 |
| (24) | 100 |
| (A) | 50 |
| No treatment | 5 |

TEXT EXAMPLE 3

The mosquito coils containing 0.3% of the following present compounds and the reference compounds were prepared according to the procedures in Formulation example 9.

Into a 6.1 m³ (183 cm cube) Peet Grady's chamber, 1.5 g of each mosquito coil were placed after igniting it at both ends. Ten minutes after the ignition, 50 female adults of common mosquitoes (*Culex pipiens pallens*) were liberated into the chamber and the combustion was further continued.

The mosquitoes were collected 20 minutes after their liberation, and were kept with feed and water. After one day, the dead and alive of mosquitoes were counted to give a mortality (Two replication).

The results are shown in Table 6

TABLE 6

| Test compound | Mortality (%) |
|---|---|
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (13) | 100 |
| (14) | 100 |
| (15) | 100 |
| (16) | 100 |
| (17) | 100 |
| (18) | 100 |
| (19) | 100 |
| (20) | 100 |
| (21) | 100 |
| (22) | 100 |
| (23) | 100 |
| (24) | 100 |
| (B) | 38 |
| (C) | 44 |
| (D) | 10 |
| (E) | 12 |
| (F) | 8 |
| (G) | 52 |
| (H) | 46 |
| No treatment | 4 |

TEST EXAMPLE 4

Ten adults (male and female, 5 adults each) of German cockroach (*Blattella germanica*) were liberated in a polyethylene cup (diameter, 9 cm) coated thinly with vaseline at the inside wall. The cup was closed with a 16-mesh nylon gauze, and placed at the bottom of an acrylic cylinder of 10 cm in inside diameter and 37 cm in height. Thereafter, 0.6 ml of each of the 0.1% oil sprays of the following present compounds and the reference compounds obtained according to Formulation example 6 was directly sprayed onto the insects by means of a spray gun at the top of the cylinder under a pressure of 0.6 atm. After 1.25 minutes elapsed, the number of the knocked-down insects was examined to obtain a percent knock-down. This test was repeated twice The results are shown in Table 7.

TABLE 7

| Test compound | Knock-down (%) |
|---|---|
| (1) | 100 |
| (2) | 100 |
| (3) | 100 |
| (4) | 100 |
| (5) | 100 |
| (6) | 100 |
| (7) | 100 |
| (9) | 100 |
| (10) | 100 |
| (11) | 100 |
| (13) | 100 |
| (19) | 100 |
| (20) | 100 |
| (22) | 100 |
| (23) | 100 |
| (B) | 20 |
| (C) | 50 |
| (D) | 5 |
| (E) | 10 |

TABLE 7-continued

| Test compound | Knock-down (%) |
|---|---|
| (F) | 15 |
| (G) | 45 |
| (H) | 35 |
| No treatment | 0 |

TEST EXAMPLE 5

The mosquito coils containing 0.3% of the following present compounds and the reference compounds were prepared according to the procedures in Formulation example 9.

Into a 6.1 m³ (183 cm cube) Peet Grady's chamber, 1.5 g of each mosquito coil were placed after igniting it at both ends. Ten minutes after the ignition, 50 ( : ♀ =1:1) adults of houseflies (*Musca domestica*, CSMA strain) were liberated into the chamber and the combustion was further continued.

The number of knock-down insects was counted 20 minutes after their liberation to calculate a percent knock-down (Two replication). The results are shown in Table 8.

TABLE 8

| Test compound | Knock-down (%) |
|---|---|
| (1) | 100 |
| (2) | 100 |
| (3) | 100 |
| (4) | 100 |
| (5) | 100 |
| (6) | 100 |
| (7) | 100 |
| (9) | 100 |
| (10) | 100 |
| (11) | 100 |
| (13) | 100 |
| (19) | 100 |
| (20) | 100 |
| (22) | 100 |
| (23) | 100 |
| (B) | 40 |
| (C) | 46 |
| (D) | 6 |
| (E) | 8 |
| (F) | 14 |
| (G) | 58 |
| (H) | 50 |
| No treatment | 2 |

TEST EXAMPLE 6

After the following compounds of the present invention and the reference compounds were each dissolved in acetone to prescribed concentrations, thus prepared solutions were respectively treated on the filter papers having an area of 6 cm×12 cm (the dose applied: 200 mg/m²).

After air-drying, the filter papers were holded double at the center and the holded papers were sealed at the both ends with a paste to make the back-like containers. Into the containers, 20 house dust mites (*Dermatophagoides farinae*) were liberated with feed. Thereafter, the open mouth of each container was pinched with a clip. The prepared test containers were placed in a chamber kept under 75% relative humidity at a temperature of 25° C. One day after the treatment, the number of the dead and alive mites was counted to calculate the mortality (Two replication).

The results are shown in Table 9.

TABLE 9

| Test compound | Mortality (%) |
|---|---|
| (1) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (13) | 100 |
| (19) | 100 |
| (20) | 100 |
| (B) | 27.5 |
| (C) | 40 |
| (D) | 17.5 |
| (E) | 10 |
| (F) | 35 |
| (G) | 47.5 |
| (H) | 42.5 |
| No treatment | 7.5 |

What is claimed is:

1. A compound represented by the formula,

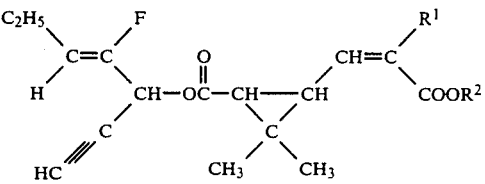

wherein $R^1$ represents hydrogen or fluorine; and $R^2$ represents methyl, ethyl, n-propyl, isopropyl, tert-butyl or cyclopropyl.

2. A compound of the formula,

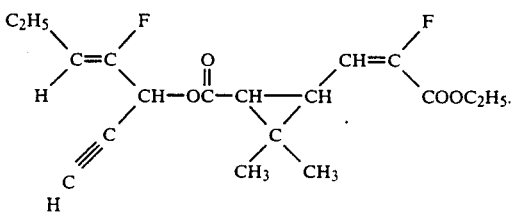

3. A compound of the formula,

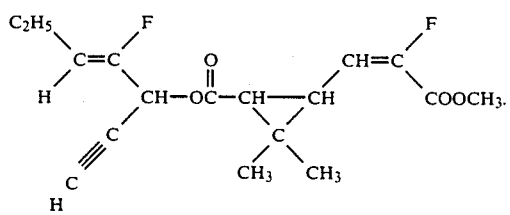

4. A compound of the formula,

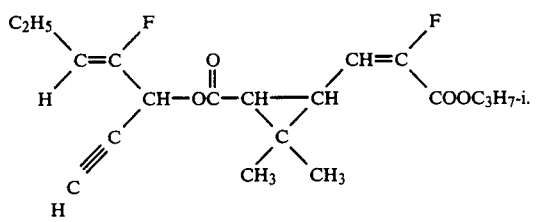

5. A compound of the formula,

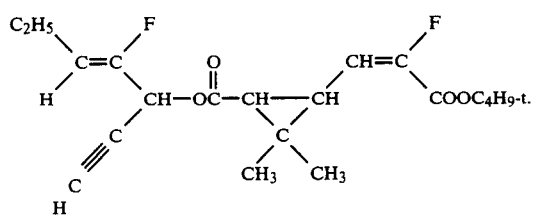

6. A compound of the formula,

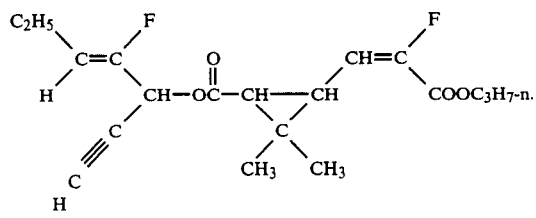

7. A compound of the formula,

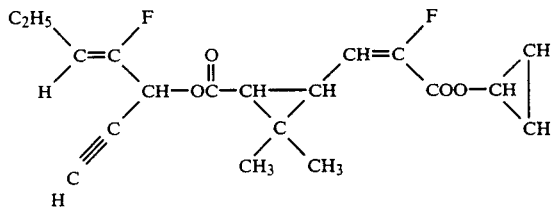

8. A compound of the formula,

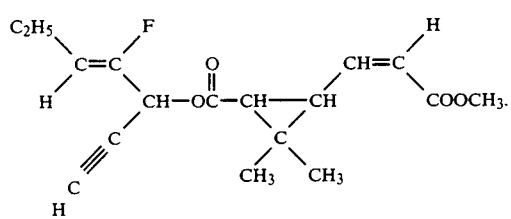

9. A compound of the formula,

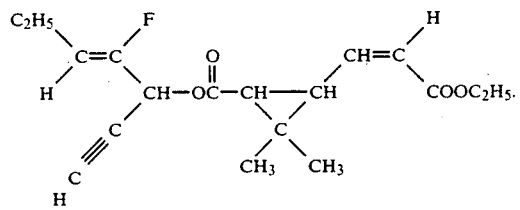

10. A compound of the formula,

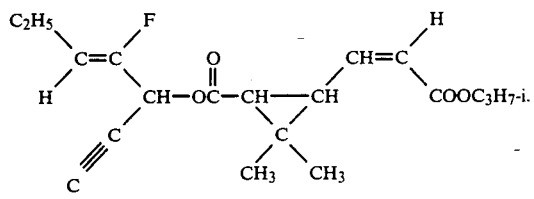

11. A compound of the formula,

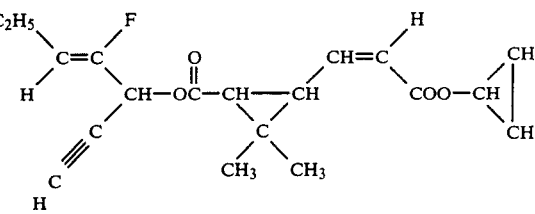

12. A compound of the formula,

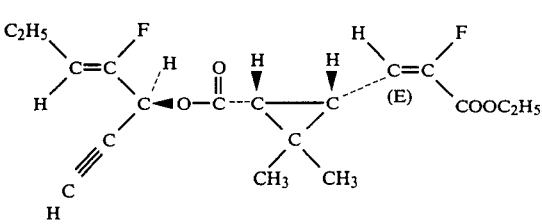

13. An insecticidal and/or acaricidal composition which composes as an active ingredient an insecticidally and/or acaricidally effective amount of a compound represented by the formula,

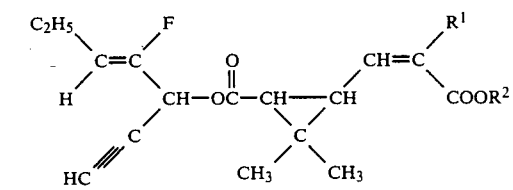

wherein $R^1$ represents hydrogen or fluorine; and $R^2$ represents methyl, ethyl, n-propyl, isopropyl, tert-butyl or cyclopropyl and a carrier.

14. A method for controlling insects and/or acarines which comprises applying an insecticidally and/or acaricidally effective amount of a compound represented by the formula,

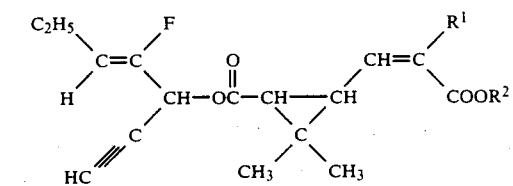

wherein $R^1$ represents hydrogen or fluorine; and $R^2$ represents methyl, ethyl, n-propyl, isopropyl, tert-butyl or cyclopropyl to the insects and/or acarines.

* * * * *